(12) United States Patent
Brandau

(10) Patent No.: US 9,551,679 B2
(45) Date of Patent: Jan. 24, 2017

(54) DEVICE FOR MEASURING THE THERMAL CONDUCTIVITY OF GAS COMPONENTS OF A GAS MIXTURE

(71) Applicant: CHEMEC GMBH, Bielefeld (DE)

(72) Inventor: Eckard Brandau, Guetersloh (DE)

(73) Assignee: CHEMEC GMBH, Bielefeld (DE)

( * ) Notice: Subject to any disclaimer, the term of this patent is extended or adjusted under 35 U.S.C. 154(b) by 0 days.

(21) Appl. No.: 14/781,312

(22) PCT Filed: Mar. 11, 2014

(86) PCT No.: PCT/DE2014/000110
§ 371 (c)(1),
(2) Date: Sep. 30, 2015

(87) PCT Pub. No.: WO2014/161521
PCT Pub. Date: Oct. 9, 2014

(65) Prior Publication Data
US 2016/0025694 A1  Jan. 28, 2016

(30) Foreign Application Priority Data
Apr. 5, 2013 (DE) .......................... 10 2013 103 388

(51) Int. Cl.
*G01N 27/18* (2006.01)
*G01K 15/00* (2006.01)
(Continued)

(52) U.S. Cl.
CPC ........... *G01N 27/185* (2013.01); *G01K 15/007* (2013.01); *G01N 25/18* (2013.01); *G01N 33/0027* (2013.01)

(58) Field of Classification Search
CPC .............................. G01N 27/18; G01N 27/185
(Continued)

(56) References Cited

U.S. PATENT DOCUMENTS 3,587,318 A  6/1971 Belugou et al.
4,164,862 A * 8/1979 Jackson ............. G01N 33/0031
73/25.03
(Continued)

FOREIGN PATENT DOCUMENTS

DE  1926250 A1  12/1969
DE  19639627 A1  4/1997
(Continued)

*Primary Examiner* — Peter Macchiarolo
*Assistant Examiner* — Nathaniel Kolb
(74) *Attorney, Agent, or Firm* — Leydig, Voit & Mayer, Ltd.

(57) ABSTRACT

A device for measuring thermal conductivity of gas components of a gas mixture in order to determine fractions of the gas components includes a plurality of thermal conductivity sensors, each thermal conductivity sensor being a component of a resistance bridge circuit and being connected to an evaluation unit associated with the device. Each thermal conductivity sensor has a heating element and an integrated temperature measuring element, which elements generate two measuring voltages ($U_{M3}$, $U_{M2}$) when the temperature of the thermal conductivity sensor changes as a result of heat dissipation by the gas mixture. Voltages are compared in the evaluation unit in order to detect measuring errors.

9 Claims, 2 Drawing Sheets

(51) Int. Cl.
*G01N 25/18* (2006.01)
*G01N 33/00* (2006.01)

(58) Field of Classification Search
USPC ........................................................ 73/25.03
See application file for complete search history.

(56) References Cited

U.S. PATENT DOCUMENTS

| | | | |
|---|---|---|---|
| 4,902,138 A | 2/1990 | Goeldner et al. | |
| 5,772,321 A | 6/1998 | Rhodes | |
| 2011/0154885 A1* | 6/2011 | Nakano | G01N 25/18 73/25.03 |
| 2013/0298638 A1* | 11/2013 | Watanabe | G01N 27/18 73/23.31 |

FOREIGN PATENT DOCUMENTS

| | | |
|---|---|---|
| DE | 19808681 A1 | 9/1999 |
| EP | 0285833 A2 | 10/1988 |
| JP | 2001050943 A | 2/2001 |

\* cited by examiner

DEVICE FOR MEASURING THE THERMAL CONDUCTIVITY OF GAS COMPONENTS OF A GAS MIXTURE

CROSS REFERENCE TO RELATED APPLICATIONS

This application is a U.S. National Phase application under 35 U.S.C. §371 of International Application No. PCT/DE2014/000110, filed on Mar. 11, 2014, and claims benefit to German Patent Application No. DE 10 2013 103 388.1, filed Apr. 5, 2013. The international application was published in German on Oct. 9, 2014, as WO 2014/161521 A1 under PCT Article 21(2).

FIELD

The invention relates to a device for measuring the thermal conductivity of gas components of a gas mixture in order to determine the fractions of the gas components by means of a plurality of thermal conductivity sensors, each thermal conductivity sensor being a component of a resistance bridge circuit and being connected to an evaluation unit associated with the device.

BACKGROUND

There are various methods in gas analysis technology for determining the gas concentrations of the components of gas mixtures.

For example, the method of gas chromatography is widespread. Here, the gas mixture to be tested is injected into a separation column that the carrier gas flows through. The substances of the gas mixture are transported by the carrier gas in the separation column, a rapid and extensive separation of the gas mixture being brought about by means of a constant temperature within the separation column or by means of a controlled temperature increase. At the outlet of the separation column, a detector identifies when one of the substances of the gas mixture leaves the separation column. The electronic signal identified by the detector can be registered as a peak and the composition of the gas mixture can be identified from this signal by means of appropriate evaluation software. The measuring set-up and execution of the procedure in gas chromatography are time consuming and structurally complex.

In addition to gas chromatography, it is generally known to use the differences in the thermal conductivity of the gases concerned in order to determine concentrations of individual gases of a gas mixture.

In principle, a resistance heating element acting as a heat source is brought up to a temperature that is higher than that of its surroundings by means of current flow. Heat from the gas to be tested is conducted via a heat conduction path defined by geometric parameters from the resistance heating element acting as a heat source to a heatsink that is kept at a constant temperature. As a result of the heat transfer from the resistance heating element to the heatsink, energy is drawn from the heat source, said energy representing a measure for the heat conductivity of the gas which can be measured using appropriate methods.

The method for identifying gas concentrations of gas mixtures by means of the heat conductivity of these gases is carried out for the various gas components using different temperatures of the resistance heating element.

In order to measure the gas concentration, on the one hand a plurality of heat conductivity sensors corresponding to the number of gas components can be used. Alternatively, the use of one heat conductivity sensor is conceivable in which the resistance heating element is heated up to different temperatures at certain intervals depending on time.

SUMMARY

In an embodiment, the present invention provides a device for measuring thermal conductivity of gas components of a gas mixture in order to determine fractions of the gas components. The device includes a plurality of thermal conductivity sensors, each of the thermal conductivity sensors being a component of a resistance bridge circuit and being connected to an evaluation unit associated with the device. Each of the thermal conductivity sensors has a heating element and an integrated temperature measuring element, which elements generate two measuring voltages when the temperature of the thermal conductivity sensor changes as a result of heat dissipation by the gas mixture. Voltages are compared in the evaluation unit in order to detect measuring errors.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
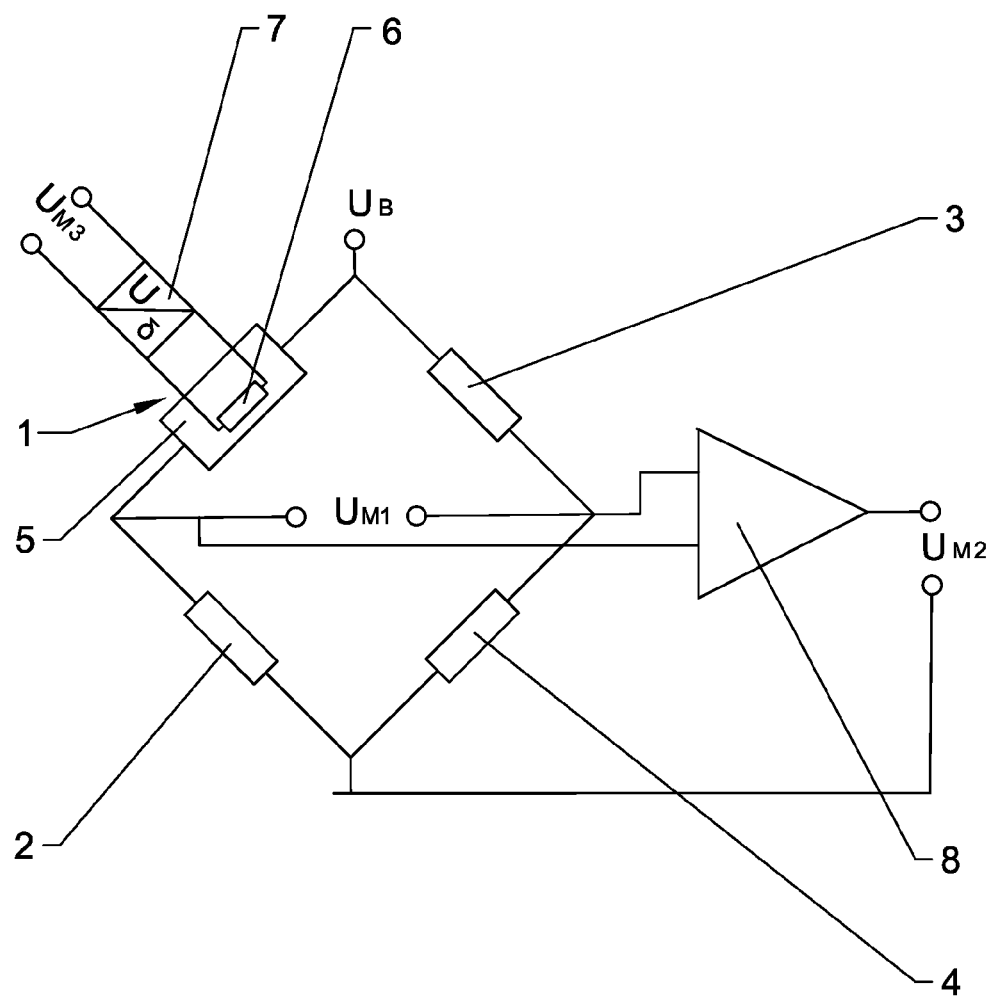
FIG. 1 is a schematic view of the construction of a thermal conductivity sensor associated with a device according to an embodiment of the invention and having downstream electronic components.

The difficulty with all systems working with heat conductivity sensors is that they have to be tested and if necessary, calibrated, using a test gas of known composition. This calibration must be repeated at regular intervals in order to ensure that the measuring device overall is working reliably and correctly. Therefore, an adequate supply of test gas must always be ensured for the users of such a device for measuring the heat conductivity of gas components of a gas mixture. This can be difficult in particular outside Europe and America since the test gases required for calibration are only produced in those geographic regions in question. Customs, transportation and safety regulations make transportation more difficult to countries in the Asian and African regions, where it must also be considered that the containers used for transporting the test gases can very likely also be abused for terrorist purposes.

Proceeding from the above-described disadvantages of the different methods for identifying gas concentrations of the components of a gas mixture, in an embodiment the invention provides a device in which, on the one hand, the use of a test gas can be omitted, and which, moreover, is constructed simply and therefore cost effectively and which, because of its construction, no longer requires any flushing phases when measuring more than one gas component by means of one single heat conductivity sensor.

In an embodiment, each thermal conductivity sensor of the device has a heating element and an integrated temperature measuring element, said elements generating two measuring voltages when the temperature of the thermal conductivity sensor changes as a result of heat dissipation by means of the gas mixture, said voltages being compared in the evaluation unit in order to identify measuring errors.

The novel structural design of the device now allows the continuous monitoring of the proper functioning of the device according to the invention in the production facility after completion of manufacturing and following an initial calibration. All measuring errors, which might occur because of the construction of the device, for example a drift of the heating element or of the temperature measuring element or the failure of one of the resistors associated with the bridge circuit, can be reliably identified by evaluating the generated measuring voltages.

It is therefore no longer necessary to ensure the correct functioning of the individual heat conductivity sensors associated with the device according to an embodiment of the invention by regular testing with a test gas whose composition is known. Therefore the necessary production, transport and testing costs associated with the test gas are dispensed with.

As a result of the integrated construction of each thermal conductivity sensor, a more robust and space-saving construction of the device according to an embodiment of the invention emerges and therefore all of the additional components that had been needed until now for the test gas calibration such as solenoid valves, pump filters, tubes and screw fixings can be omitted. The novel device can therefore be directly implied into an appropriate gas pipeline, the reliability of the gas analysis increasing significantly as a result of the device being maintenance-free.

With respect to a robust and maintenance-free construction of the device according to an embodiment of the invention, it can be advantageous to construct the heating element as a PT-20 sensor and to use a PT-100 sensor for the temperature measuring element. The elements in question can be combined without difficulty to form a thermal conductivity sensor. In the process, the thermal conductivity sensor can advantageously be constructed on a central ceramic body, which consists of silicon oxide for example. Conductor tracks, which form the PT-20 and PT-100 sensors and are made from a paste containing platinum are applied to this ceramic body by screen printing in a thin-film process. In order to protect the platinum conductor tracks on the ceramic body, said body is provided with a glass coating such that chemical reactions between the platinum paste and aggressive components that are potentially to be detected in a gas mixture can be ruled out reliably.

Moreover, with respect to the electrical construction of the device according to an embodiment of the invention, it can be advantageous to provide each conductivity sensor with a temperature voltage transformer. The electrical construction is additionally completed by a differential amplifier, which converts the bridge voltage identified inside the bridge circuit into a mass-related signal.

The schematic circuit diagram in FIG. 1 shows the construction of a thermal conductivity sensor by means of which the concentration of a component of a gas mixture can be measured.

The overall device for measuring the conductivity of gas components of a gas mixture in order to determine the fractions of the gas components for N fractions consists of N thermal conductivity sensors. Assigned to the thermal conductivity sensors is a central evaluation unit, in which the measuring voltages identified by the individual thermal conductivity sensors are assigned, compared and evaluated.

The evaluation unit has been omitted from the drawing because it is not a primary part of the device that is essential to an embodiment of the invention.

The basic construction of each thermal conductivity sensor consists of a resistance bridge circuit in which a thermal conductivity sensor is arranged instead of a resistor R1. This thermal conductivity sensor consists of a heating element, for example in the form of a PT-20 sensor, and a temperature measuring element, for example in the form of a PT-100 sensor, as an integral component of the thermal conductivity sensor, which in its entirety is denoted by 1. The other resistors are denoted by 2, 3 and 4.

A temperature/voltage transformer 7 is assigned to the thermal conductivity sensor 1 and generates a measuring voltage $U_{M3}$. A voltage $U_B$ is applied to the bridge circuit during operation of the device according to the invention. The voltage $U_B$ causes the heating element 5 to heat up to a temperature $T_{Heater}$ determined by means of calibration in the context of manufacturing. The temperature $T_{Heater}$ for each thermal conductivity sensor of the device according to the invention is tailored to the gas component to be measured of the gas mixture and therefore differs.

The temperature of the heating element 5 is measured by means of the temperature measuring element 6 and outputted by the measuring voltage $U_{M3}$. While the device according to the invention is operating, some of the heat generated by the heating element 5 is dissipated via the measuring gas which passes over the thermal conductivity sensor. The higher the thermal conductivity of the gas passing over, i.e. the more heat that is dissipated, the cooler the surface of the heating element 5. The bridge voltage $U_{M1}$ changes proportionally to the thermal conductivity of the gas and is converted into a mass-related measuring voltage $U_{M2}$ using the downstream differential amplifier 8.

The entire device functions correctly provided that the voltages $U_{M2}$ and $U_{M3}$ change proportionally to one another. This is monitored continuously by means of the evaluation unit. The device according to the invention therefore checks itself constantly.

If a difference occurs between the two measuring voltages, there is a malfunction of the device. Regular calibration and testing using a test gas can therefore be dispensed with. A malfunction can have various causes: Drift of the bridge voltage $U_B$: Using a precision AD converter, the respective bridge voltages are constantly checked using a multiplexer and readjusted accordingly. Drift of the heating element 7: Should this error occur, ambient air is applied to the heating element and the bridge voltage $U_B$ is readjusted to the extent that the base temperature $T_{Heater}$ in air is equivalent to the stored base temperature in the software of the evaluation unit. Drift of the temperature measuring element: In the event that the temperature measuring element 6 drifts, the corresponding temperature coefficient of the temperature measuring element 6 changes. In order to check, ambient air is applied to the thermal conductivity sensor and the base temperature $T_{Heater}$ is measured. Then all operating voltages are switched off so that each of the heating elements, associated with the device, of the thermal conductivity sensors cool down to the ambient temperature. All temperature measuring elements must then display the same temperature. If the differences between the base temperatures can be compensated below the ambient temperature by means of iterative changing of the zero point and amplification of the temperature voltage transformer 7, the device according to the invention can continue to be used. Should this not be the case, the entire device must be replaced. Drift of the temperature voltage transformer 7: Such a malfunction can be checked with the aid of a precision diode and, if appropriate, readjusted. Drift of the differential amplifier 8: Such a malfunction can be detected clearly and can be compensated by readjusting the differential amplifier 8 in ambient air. If, in rare cases, the failure of a resistor 2, 3 or 4 is registered, the corresponding thermal conductivity sensor is likewise to be replaced.

Figure 2:
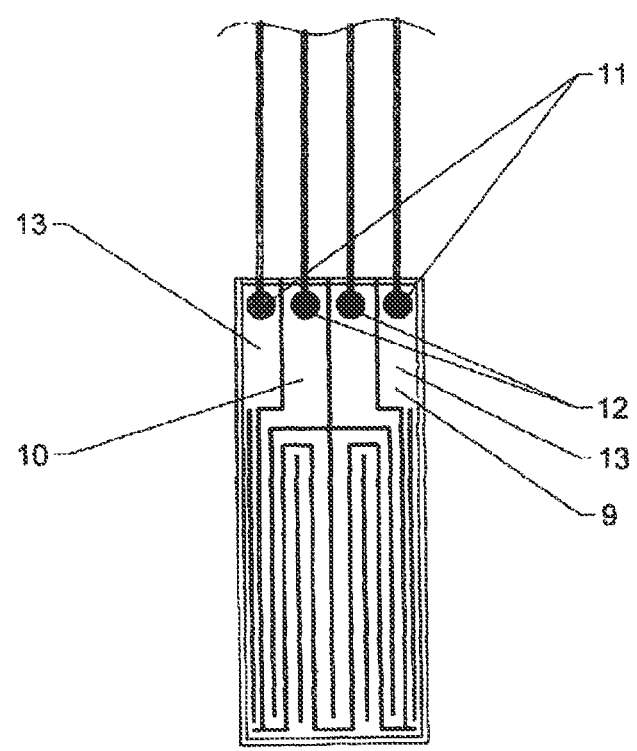
FIG. 2 is the view of a thermal conductivity sensor with which the device according to an embodiment of the invention can be constructed.

The practical construction of a thermal conductivity sensor 1 associated with the device according to the invention is illustrated in FIG. 2. The drawing shows a ceramic base body 9, which is an essential element of the thermal conductivity sensor. The base body can advantageously consist of silicon oxide and the top thereof is coated with conductor tracks 10 made of a paste containing platinum. The separation of the conductor tracks 10 is illustrated in FIG. 2 by black dividing lines.

As can be seen from the drawing, the base body 9 has two connection points 11 and two connection points 12, which are each associated with a conductor track 10 and 13 respectively. The base body shown has a base surface of 5×2 mm and can therefore be integrated without difficulty in a gas pipeline even if a plurality of thermal conductivity sensors are used. Further elements for measuring the thermal conductivity of individual gas components of a gas mixture for determining the fractions of the gas components are not necessary, in contrast to conventional measuring devices. The evaluation unit can be constructed separately.

Furthermore, it should be noted that, due to the simultaneous use of N heat conductivity sensors for N fractions of a gas mixture, flushing phases between the measurements of individual components, which phases are necessary in the case of some conventional measuring devices, can be dispensed with.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS

1 Heat conductivity sensor
 2 Resistor
 3 Resistor
 4 Resistor
 5 Heating element
 6 Temperature measuring element
 7 Temperature/voltage transformer
 8 Differential amplifier
 9 Base body
10 Conductor track
11 Connection point
12 Connection point
13 Conductor track

The invention claimed is:

1. A device for measuring thermal conductivity of gas components of a gas mixture in order to determine fractions of the gas components, the device comprising:
 a plurality of thermal conductivity sensors, each of the thermal conductivity sensors comprising only one resistance bridge circuit and being connected to an evaluation unit associated with the device,
 wherein each of the thermal conductivity sensors has differential amplifier, a heating element and an integrated temperature measuring element, wherein the heating element and the temperature measuring element are integrally connected and the heating element comprises a single leg of the bridge circuit, the elements being configured to generate two measuring voltages when the temperature of the thermal conductivity sensor changes as a result of heat dissipation by the gas mixture, one of the measuring voltages output by the temperature measuring element and representative of the temperature of the heating element and the other one of the measuring voltages being generated from the differential amplifier being configured to convert a bridge voltage of the resistance bridge circuit into a mass-related voltage signal, and
 wherein the evaluation unit is configured to compare the two measuring voltages so as to detect measuring errors.

2. The device according to claim 1, wherein the heating element is a PT-20 sensor.

3. The device according to claim 1, wherein the temperature measuring element is a PT-100 sensor.

4. The device according to claim 1, wherein the thermal conductivity sensor includes a base body on the surface of which the heating element and the temperature measuring element are applied in the form of conductor tracks by screen printing in a thin-film process.

5. The device according to claim 4, wherein the conductor tracks are covered with a glass coating.

6. The device according to claim 1, wherein the thermal conductivity sensors include a ceramic base body.

7. The device according to claim 6, wherein the base body includes silicon oxide.

8. The device according to claim 6, wherein the base body includes a top surface coated with platinum conductor tracks that are covered with a glass coating.

9. The device according to claim 1, wherein the evaluation unit is configured to detect the measuring errors by monitoring whether the two measuring voltages change proportionally to one another.

* * * * *